United States Patent [19]  [11] 4,188,830
Mason et al.  [45] Feb. 19, 1980

[54] APPARATUS FOR EXAMINING STRUCTURES USING STIMULATED ACOUSTIC EMISSION

[75] Inventors: Warren P. Mason, West Orange; Daniel N. Beshers, Tenafly, both of N.J.; John T. Kuo, Blauvelt, N.Y.

[73] Assignee: The United States of America as represented by the Secretary of the Army, Washington, D.C.

[21] Appl. No.: 954,264

[22] Filed: Oct. 24, 1978

[51] Int. Cl.² .............................................. G01N 3/38
[52] U.S. Cl. ..................................................... 73/801
[58] Field of Search ................ 73/801, 802, 587, 583, 73/662, 577, 578

[56] References Cited
U.S. PATENT DOCUMENTS

| | | | |
|---|---|---|---|
| 2,014,410 | 9/1935 | Pierce | 73/662 X |
| 2,559,565 | 10/1941 | Hutcheson | 73/662 |
| 3,529,465 | 9/1970 | Kleesattel et al. | 73/577 |
| 3,985,024 | 10/1976 | Horak | 73/587 |
| 4,089,224 | 5/1978 | Scott et al. | 73/801 X |

*Primary Examiner*—Jerry W. Myracle
*Attorney, Agent, or Firm*—Nathan Edelberg; Robert P. Gibson; Saul Elbaum

[57] ABSTRACT

A vibrator is held in contact with a structure undergoing testing, such as an airplane wing. Vibrations are distributed through the structure and structural defects such as fissures will respond by emitting an acoustic signal. The acoustic signal may occur over a wide frequency range. A pick-up having a crystal transducer also makes contact with the surface of the structure to detect acoustic emissions. The crystal has a wide band response capable of detecting structural defect acoustic emissions. The pick-up has electrical leads connected thereto so that the acoustic emissions are converted to electrical signals which may be recorded or viewed on an oscilloscope. Movement of the pick-up across the surface of the structure will help determine the location of the structural defect.

6 Claims, 1 Drawing Figure

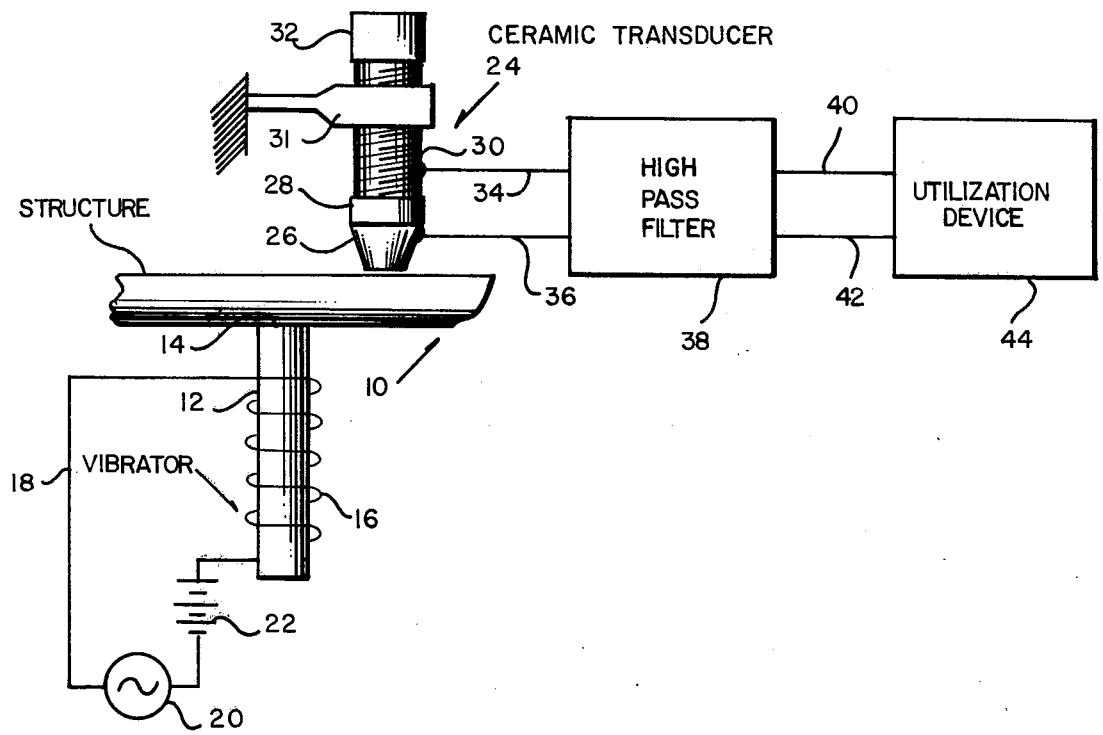

APPARATUS FOR EXAMINING STRUCTURES USING STIMULATED ACOUSTIC EMISSION

RIGHTS OF THE GOVERNMENT

The invention described herein may be manufactured, used, and licensed by or for the United States Government for governmental purposes without the payment to us of any royalty thereon.

FIELD OF THE INVENTION

The present invention relates to non-destructive testing of structures and more particularly to a method and apparatus for such testing of metal structures utilizing low frequency vibratory energy.

BRIEF DESCRIPTION OF THE PRIOR ART

The testing for flaws in structures, particularly metal structures, is extremely important for many applications including the detection of flaws in munition casings and aircraft structures. It is desirable to test such structures non-destructively. By that it is meant that there is no destruction of the structure as a result of the tests so that an acceptable structure may be used after testing. The current systems for studying acoustic emissions from structures utilize slowly increasing near-static stress to stimulate the emission events. They are limited to observations on the first loading to a given stress level. This is an irreversible process known as the Kaiser effect.

BRIEF DESCRIPTION OF THE PRESENT INVENTION

The present invention utilizes a vibrator which is maintained in contacting relationship with a structure undergoing testing. The vibrations are transmitted through the structure and structural defects will respond to the vibrational stimulation by emitting acoustical signals over a fairly broad frequency range. The emissions are caused by frictional rubbing at the interface of microscopic confronting surfaces at the defect. The frequency of response varies and depends upon the material undergoing testing and the nature of the defect. Accordingly, any acoustic pick-up must be capable of sensing the emissions from a defect over a wide frequency range.

The present invention has the following salient advantages: it eliminates the prior art requirement for any mechanical testing machine which may emit random noises which will interfere with measuring and testing. The vibrator as used in connection with the present invention has very little extraneous signal associated with it and the little involved is cyclic and easily determined. Another advantage of the invention is the recognition of a much higher sensitivity in signal detection. Further, a very wideband frequency response is obtained which permits many kinds of signals to be detected. Still further, the construction of the present invention lends itself to portability for field use.

BRIEF DESCRIPTION OF THE FIGURE

The above-mentioned objects and advantages of the present invention will be more clearly understood when considered in conjunction with the accompanying drawing, in which:

The FIGURE is a diagrammatic representation of the present invention as operational in the testing of a structural member such as an airplane wing.

DETAILED DESCRIPTION OF THE INVENTION

Referring to the FIGURE, reference numeral 10 generally indicates a structure undergoing testing, such as an illustrated airplane wing. The detection of structural flaws is sought which will be achieved by non-destructive testing. A vibrator may be fabricated from a magnetostrictive rod 12 which has an upper end thereof in stress contact with surface 14 of structure 10. A coil 16 is wrapped around the magnetostrictive rod 12, the coil having its terminals connected in series with an AC generator 20 and a DC source 22 through lead 18. The AC generator imposes a cyclical signal on a DC component, the latter generated by the DC source 22, so that sufficient magnetostrictive vibrating motion is imparted to the structure 10 by the contacting rod 12. In lieu of a magnetostrictive vibrator, an electromagnetic version could be used. The AC generator will generate an acoustic signal. The components described thus far individually constitute prior art.

Also in contact with the structure 10 is a signal pick-up which is generally referred to as a ceramic transducer 24. The lower portion of the transducer 24 includes a metallic frusto-conical member which will be referred to as a cone 26. The lower edge of the cone is flattened so that better contact with the confronting surface of the structure 10 may be made. A ceramic disc 28 is suitably attached to the upper end of the cone 26 and is fabricated from a ceramic material known in the trade as PZT ceramic. This type of ceramic is capable of a wideband frequency response which is the nature of the emissions from structural defects undergoing vibration within the structure 10. Attached to the upper surface of the ceramic disc 28 is a threaded brass rod 30 that is secured within a mating threaded holder 31. The threads enable the cone 26 to be adjustably positioned for making contact with the structure 10.

In order to dampen lower frequency signals which may be ascribed to the vibrating motion, a termination of heavy metal, such as a lead termination 32, is suitably attached to the upper edge of the brass rod 30. The noise emitted from a structural defect such as a fatigue crack or other imperfection may be anywhere in frequency from the low kilohertz region up to the megahertz region and hence requires a wideband pick-up device to determine the source of the noise while suppressing the applied vibration signal. Electrical leads 34 and 36, respectively connected to the brass rod 30 and cone 26, feed these wideband noise emission signals from the ceramic disc 28 to a conventional high pass filter 38 which filters out vibrational signals from the source. Leads 40 and 42 are connected between the output of the high pass filter 38 and an appropriate measuring or detecting utilization device 44. This may include an oscilloscope, voltmeter, recorder or spectrum analyzer. By using several ceramic transducers 24, a triangulation scheme may be employed to locate a detected imperfection.

We wish it to be understood that we do not desire to be limited to the exact details of construction shown and described, for obvious modifications can be made by a person skilled in the art.

We claim the following:

1. A system for detecting structural flaws comprising:
    vibrating means engaging a structure for causing acoustic emissions produced by alternating stresses at a structural flaw;

means for contacting the structure;

a transducing member attached to the contacting means for converting the emissions to electrical signals;

means for mounting the transducing member and the contacting means thereto thus enabling position adjustment of the contacting means relative to the structure; and connecting means connected in circuit with the transducing member for feeding the converted electrical signals to a utilization device.

2. The subject matter set forth in claim 1 wherein the vibrating means comprises a magnetostrictive member;

a coil wrapped around the magnetostrictive member; and sources of AC and DC voltages connected in circuit with the coil.

3. The subject matter set forth in claim 1 wherein the vibrating means comprises:

an electromagnetic device and power means for cyclically driving the electromagnetic device.

4. The subject matter set forth in claim 1 wherein the transducing member is fabricated from ceramic material.

5. The subject matter set forth in claim 4 wherein the connecting means are leads connected at first ends thereof to the contacting means and the mounting means, and further wherein second ends of the leads are connected to a high pass filter for filtering out signals corresponding to the vibration.

6. The subject matter set forth in claim 5 wherein a relatively heavy means is attached to the mounting means to dampen vibration of the contacting means, transducing member and mounting means.

* * * * *